(12) United States Patent
Chen et al.

(10) Patent No.: US 7,725,165 B2
(45) Date of Patent: May 25, 2010

(54) METHOD AND APPARATUS FOR VISUALIZING ANATOMICAL STRUCTURES

(75) Inventors: David Chen, Wrentham, MA (US); Tuba Sahin, Hanover, NH (US)

(73) Assignee: M2S, Inc., West Lebanon, NH (US)

( * ) Notice: Subject to any disclaimer, the term of this patent is extended or adjusted under 35 U.S.C. 154(b) by 1103 days.

(21) Appl. No.: 11/296,103

(22) Filed: Dec. 7, 2005

(65) Prior Publication Data

US 2006/0184006 A1   Aug. 17, 2006

Related U.S. Application Data

(60) Provisional application No. 60/634,010, filed on Dec. 7, 2004.

(51) Int. Cl.
*A61B 6/00* (2006.01)
(52) U.S. Cl. ...................... 600/425; 382/128
(58) Field of Classification Search .............. 378/42; 382/128, 131, 285, 293–300; 600/424–427; 623/1.11

See application file for complete search history.

(56) References Cited

U.S. PATENT DOCUMENTS

| | | | |
|---|---|---|---|
| 5,274,551 A | 12/1993 | Corby, Jr. | |
| 5,737,506 A | 4/1998 | McKenna et al. | |
| 5,825,908 A * | 10/1998 | Pieper et al. | 382/131 |
| 6,151,404 A | 11/2000 | Pieper | |
| 6,711,432 B1 | 3/2004 | Krause et al. | |
| 6,711,433 B1 * | 3/2004 | Geiger et al. | 600/431 |
| 7,432,924 B2 * | 10/2008 | Ohishi | 345/419 |
| 2005/0147283 A1 | 7/2005 | Dwyer et al. | |

\* cited by examiner

*Primary Examiner*—Brian Casler
*Assistant Examiner*—Parikha S Mehta
(74) *Attorney, Agent, or Firm*—Pandiscio & Pandiscio

(57) ABSTRACT

Apparatus and method for producing a virtual road map of a patient's vascular anatomy comprising a virtual 3D model of the patient's vascular and bony structure in proper registration with one another, a fluoroscope for providing real-time images of the bony structure of the patient, registration apparatus for placing the virtual 3D model in proper registration with the patient space of the fluoroscope, bone mask subtraction apparatus for generating a bone mask of the bony structure, and subtracting the same from the real-time images, whereby to create modified fluoroscope images omitting bony structure, and image generating apparatus for generating the virtual road map comprising a composite image combining (i) images of the virtual 3D structure representing the vascular structure, and (ii) modified fluoroscope images omitting bony structure, wherein the images of the virtual 3D structure representing vascular structure are in proper registration with the modified fluoroscope images omitting bony structure.

12 Claims, 5 Drawing Sheets

METHOD AND APPARATUS FOR VISUALIZING ANATOMICAL STRUCTURES

REFERENCE TO PENDING PRIOR PATENT APPLICATION

This patent application claims benefit of pending prior U.S. Provisional Patent Application Ser. No. 60/634,010, filed Dec. 7, 04 by David Chen et al. for INTRAOPERATIVE C-ARM FLUOROSCOPE DATA FUSION SYSTEM, which patent application is hereby incorporated herein by reference.

FIELD OF THE INVENTION

This invention relates to medical systems in general, and more particularly to medical systems for visualizing anatomical structures.

BACKGROUND OF THE INVENTION

In current medical practice, in order to obtain real-time visualization of the vascular system of a patient, a fluoroscope may be used. The fluoroscope is an X-ray machine which can image moving (or non-moving) internal anatomy. The most common type of fluoroscope found in a vascular surgical suite is the "C-arm" fluoroscope. In the C-arm fluoroscope, the X-ray source and the X-Ray detector are connected together by a "C"-shaped gantry that can rotate (with two degrees of freedom) around the patient's body. See, for example, FIG. 1.

Because the imaging energy used in a fluoroscope comes from an X-ray tube, the anatomy that is X-ray opaque (e.g., bone) is highly visible, while tissue that is X-ray transparent (e.g., soft tissue, such as blood vessels) is substantially invisible. As a result, a contrast agent (e.g., iodine-based) is typically used to enhance the visibility of the lumen of the blood vessel. In this respect it will be appreciated that the contrast agent must be administered in sufficient quantity, and at the right time relative to the moment of X-ray capture, in order to produce good images.

Through the use of a C-arm fluoroscope and such contrast agents, a surgeon can see enough of a patient's vascular anatomy to perform procedures such as the endoluminal repair of an abdominal aortic aneurysm (AAA). Such endoluminal repairs are typically performed using a stent graft which is advanced to the surgical site through a catheter. The catheter is commonly inserted into the femoral artery and then advanced up the femoral artery, through the iliac branch and along the aorta to the site of the aneurysm.

During the endoluminal repair procedure, the stent graft must be carefully positioned within the aorta so as to avoid blocking the renal arteries. In most modern fluoroscope systems, the renal arteries can be seen with a "road map" view, in which the blood vessels are enhanced so as to appear white, and the bones of the spine are digitally removed, i.e., through a subtraction process, so as to render the view more clearly.

To produce the road map view, the spinal bones are first imaged using fluoroscopy so as to produce a "mask" image. In this mask image, the bones appear dark and the blood vessels are effectively invisible (because no contrast agent is used). Then, a fluoroscopic image is taken using a contrast agent so that both the blood vessels and spinal bones are dark. The mask image is then "subtracted" from the contrast image so as to produce a resulting image which includes only the dark, contrast-enhanced regions of the blood vessels. The pixel values in this resulting image are then digitally inverted, so that the dark blood vessels become white, whereby to produce the final image shown in FIG. 2.

While effective, the foregoing process requires the generation of multiple images, the use of a contrast agent which may be deleterious to the patient's health, the processing associated with image subtraction, etc.

Thus, it would be desirable to provide a new visualization process which does not require the use of the contrast agent, among other things.

SUMMARY OF THE INVENTION

These and other objects are addressed by the present invention, which comprises a Virtual Road Mapping System which is adapted to produce a "virtual road map" image of the patient's vascular anatomy without requiring the use of a contrast agent. The present invention uses data from pre-acquired Computer Tomography (CT), CT-angiography or Magnetic Resonance Angiography (MRA) to generate virtual images of the patient's blood vessel anatomy, and these virtual images are merged with the actual images from the fluoroscope so as to provide a composite view. This composite view essentially forms a virtual road map for the surgeon.

In one form of the present invention, there is provided an apparatus for producing a virtual road map of a patient's vascular anatomy for use by a surgeon while conducting a procedure on the patient's vascular anatomy, the apparatus comprising:

a virtual 3D model of the patient's anatomy, wherein the virtual 3D model comprises a virtual 3D structure representing bony structure of the patient and a virtual 3D structure representing vascular structure of the patient, with the virtual 3D structure representing bony structure of the patient being in proper registration with the virtual 3D structure representing vascular structure of the patient;

a fluoroscope for providing real-time images of the bony structure of the patient and a surgical device being used in the procedure;

registration apparatus for placing the virtual 3D model in proper registration with the patient space of the fluoroscope;

bone mask subtraction apparatus for (i) generating a bone mask of the bony structure of the patient, and (ii) subtracting the same from the real-time images provided by the fluoroscope, whereby to create modified fluoroscope images omitting bony structure; and image generating apparatus for generating the virtual road map, wherein the virtual road map comprises a composite image combining (i) images of the virtual 3D structure representing vascular structure of the patient, and (ii) modified fluoroscope images omitting bony structure, wherein the images of the virtual 3D structure representing vascular structure of the patient are in proper registration with the modified fluoroscope images omitting bony structure.

In another form of the present invention, there is provided an apparatus for visualizing a surgical site, the apparatus comprising:

data fusion apparatus for merging (i) virtual images of vascular structures of a patient, wherein the virtual images are created from pre-acquired scan data; and (ii) real-time images acquired by a fluoroscope.

In another form of the present invention, there is provided a method for visualizing anatomical structures, the method comprising the steps of:

(1) processing pre-acquired scanned patient-specific data so as to produce a virtual 3D model of appropriate anatomical structures, wherein processing is effected so that separate views of the bone and blood flow structures can be generated;

(2) positioning a C-arm fluoroscope with standard Anterior-Posterior (AP) orientation relative to the patient;

(3) conducting fluoroscopic imaging so as to provide good images of the patient's bone structure;

(4) overlaying, on top of the fluoroscopic images, virtual images from the virtual 3D model, with those images representing only the patient's bone structure;

(5) placing the virtual images of the patient's bone structure generated from the virtual 3D model in proper registration with the fluoroscope images of the patient's bone structure, whereby the coordinate system of the virtual 3D model is correlated to the coordinate system of the fluoroscope;

(6) imaging the patient's bone structure using fluoroscopy so as to create a standard mask image of the patient's bone structure;

(7) turning off the virtual images of the virtual bone structure and turning on the virtual images of the blood flow structure, so as to show the blood flow structure from the virtual 3D model overlaid on top of the fluoroscopic images in a semi-transparent mode, whereby to provide a composite view simultaneously showing the patient's blood flow structure from the virtual 3D model and the patient's bone structure from the fluoroscopic images;

(7A) using the mask image to subtract out the bone structure from the composite view, whereby to produce the virtual road map which will be used by the surgeon.

In another form of the present invention, there is provided a method for visualizing a surgical site, the method comprising:

pre-acquiring scan data of the surgical site; and merging (i) virtual images of vascular structures, wherein the virtual images are created from pre-acquired scan data; and (ii) real-time images acquired by a fluoroscope.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PRESENT INVENTION

In order to better understand the concepts of the present invention, it can be helpful to first consider a standard Abdominal Aortic Aneurysm (AAA) patient-specific study as produced by Medical Metrx Solutions of West Lebanon, N.H. (MMS) and utilized in the MMS Preview™ System.

With the MMS Preview™ System, a virtual, patient-specific 3D model (i.e., the patient-specific AAA study) is constructed from scan data (e.g., CT, CT-angiography, MRA, etc.) to represent the patient's anatomy. More specifically, the virtual 3D model comprises a plurality of virtual objects which are placed in proper registration with one another and which represent specific anatomical objects (e.g., bones, blood vessels, blood flow, etc.). These virtual objects can be grouped together (as appropriate) into virtual, 3D structures, whereby to represent specific anatomical structures or systems (e.g., vascular systems, bone structures, etc.). By way of example, one set of virtual objects is grouped together to define a virtual structure which represents the patient's vascular anatomy, including blood flow (the aorta, the iliac branches, the renal arteries, etc.), thrombus-filled regions and calcified plaques. Another set of virtual objects is grouped together to define a virtual structure which represents the bones of the patient's spine. The virtual 3D model is configured so that the various objects and/or structures can be separately displayed as desired. See, for example, the left side of FIG. 3, which shows, among other things, a virtual structure representing the patient's vascular structure, and a virtual structure representing the bones of the patient's spine. It should be appreciated that, in the typical patient anatomy, the renal arteries are generally aligned in the proximity of the L1/L2 vertebrae when viewed in the Anterior-Posterior (AP) view.

For the purposes of the Virtual Road Mapping System of the present invention, it is desirable that the virtual structures representing the spine and renal arteries be capable of being visualized separately and independently. Such visualization may be effected through standard modeling and visualization techniques such as, but not limited to, surface rendering, shaded surface display, volume rendering, etc. In fact, such separate and independent visualization of various virtual structures is easily achieved using the virtual 3D model of the MMS Preview™ System.

The Virtual Road Mapping system is configured to produce a composite image created by merging (i) virtual images generated from the virtual 3D model created from the pre-acquired CT-derived spine and blood flow data, and (ii) the real-time images obtained from the fluoroscope.

Figure 1:
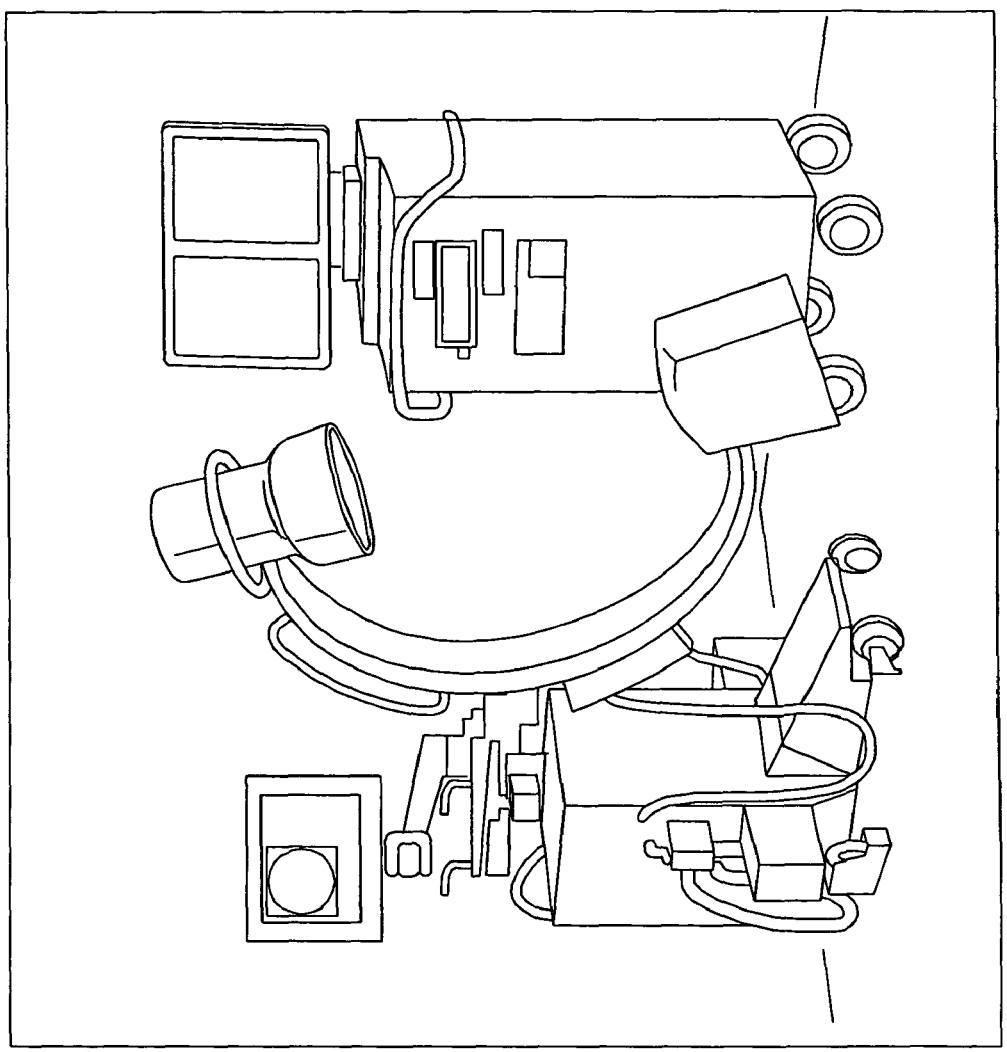
FIG. 1 is schematic view showing a prior art C-arm fluoroscope.
Figure 2:
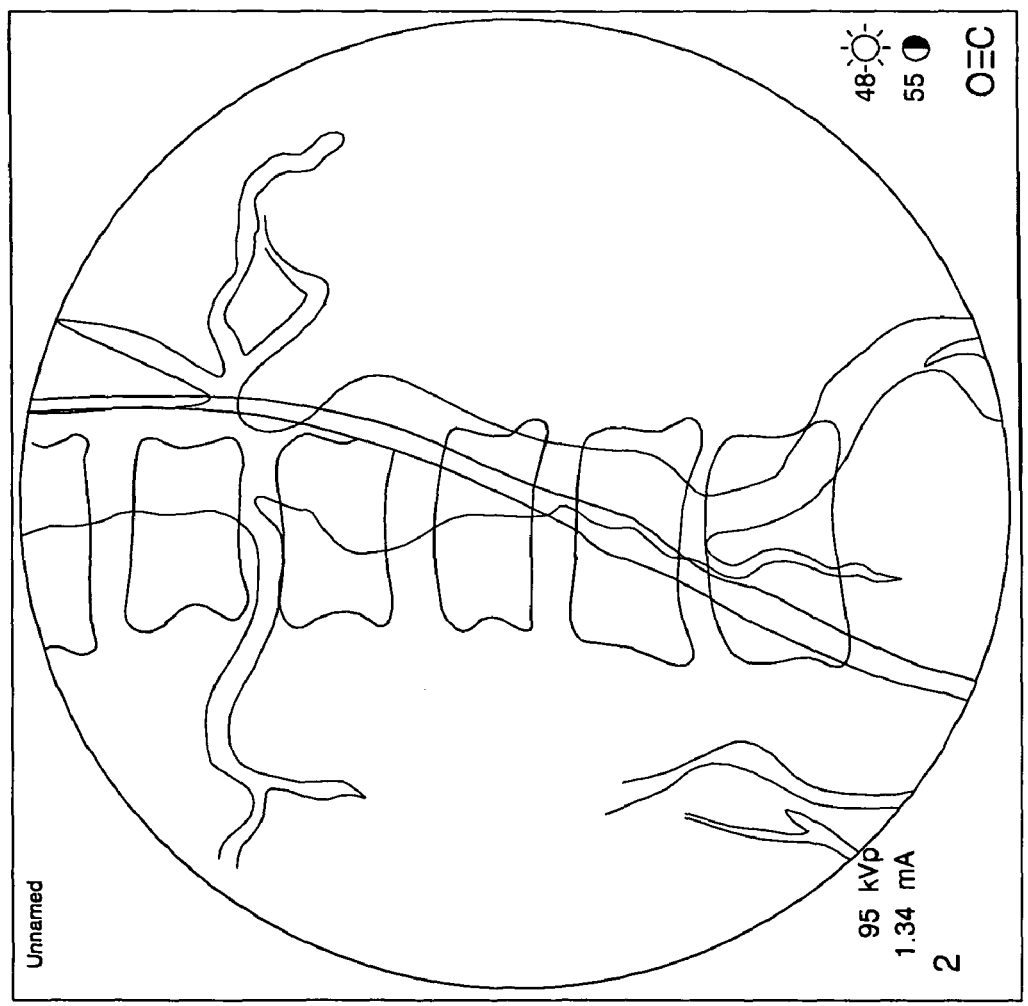
FIG. 2 is a schematic view showing a road map view generated using a prior art system.
Figure 3:
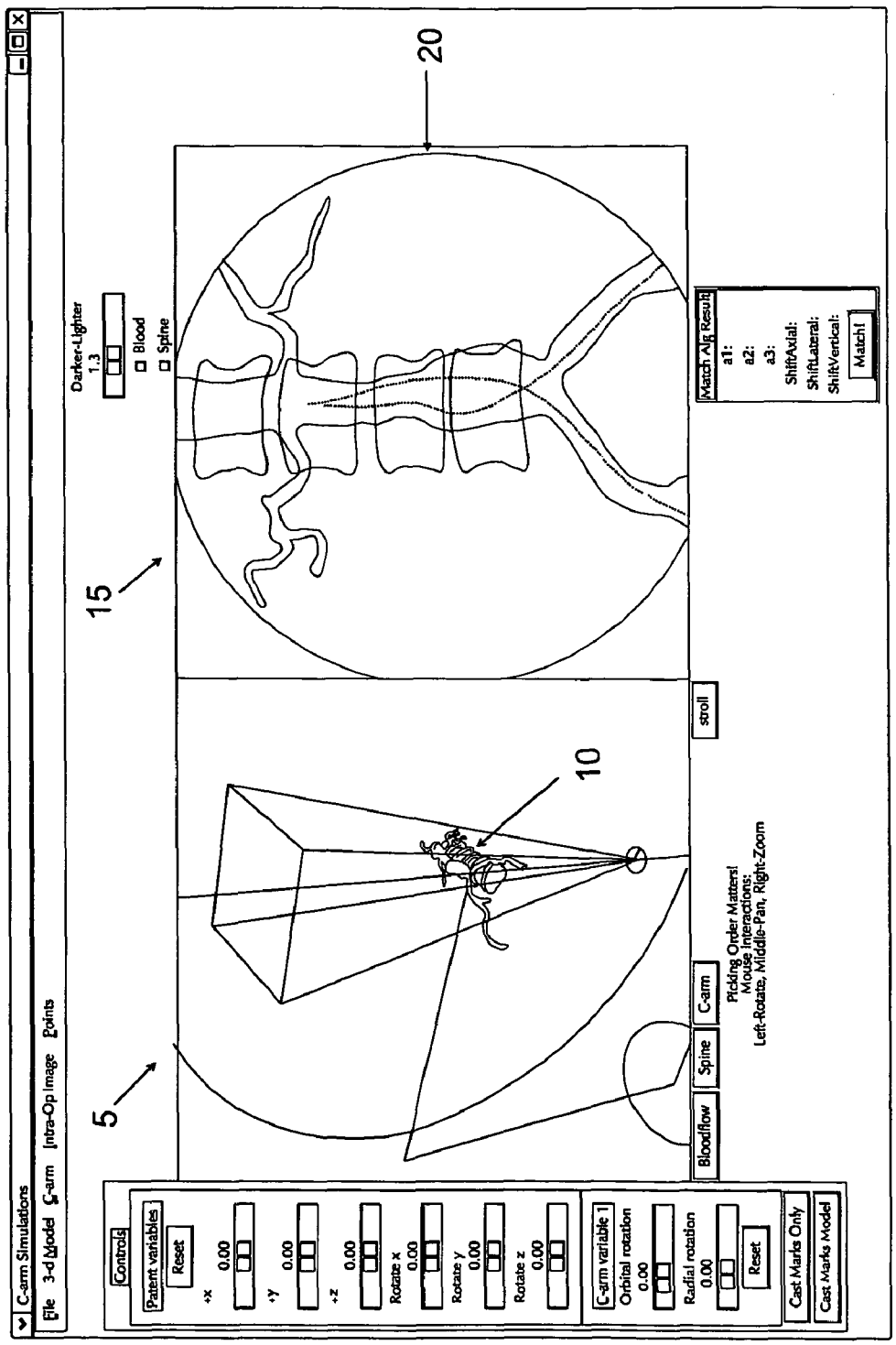
FIG. 3 is a schematic view generated in accordance with the present invention, showing (i) the patient's CT-derived spine and blood flow data visualized in a virtual image, along with a 3D geometric representation of the system's C-arm fluoroscope (left side of FIG. 3); and (ii) the composite image produced by datafusing the real-time image from the C-arm fluoroscope with the virtual image generated from the patient's CT-derived spine and blood flow data (right side of FIG. 3)

More particularly, in one preferred embodiment of the present invention, the Virtual Road Mapping system is preferably configured so that it can produce two different displays in side-by-side relation (see FIG. 3). The first display 5 (left side of FIG. 3) shows the patient's CT-derived spine and blood flow data visualized in a virtual image 10, along with the 3D geometric representation of the system's C-arm fluoroscope. The second display 15 (right side of FIG. 3) shows the image 20 produced by datafusing the real-time image from the C-arm fluoroscope with the virtual image generated from the patient's CT-derived spine and blood flow data. Note that this overlay image is designed to match, as closely as possible, the imaging geometry of the C-arm fluoroscope in terms of the produced viewpoint and field of view.

In one preferred form of the present invention, the system is configured to produce the virtual road map as follows.

(1) Pre-acquired CT, CT-Angiography or MRA patient-specific data is processed so as to produce a 3D model of appropriate anatomical structures. Preferably the virtual objects are grouped such that separate views of the spine and blood flow lumen can be generated. By way of example but not limitation, this can be done using a standard MMS AAA study and the MMS Preview™ System. See also, for example, U.S. Pat. No. 5,737,506; U.S. Pat. No. 6,151,404; U.S. Pat. No. 5,825,908; and pending U.S. patent application Ser. No. 10/985,199, filed Nov. 10, 2004 by Jeff Dwyer et al. for ANATOMICAL VISUALIZATION AND MEASUREMENT SYSTEM; which documents are hereby incorporated herein by reference.

(2) A C-arm fluoroscope is positioned with standard Anterior-Posterior (AP) orientation in the general abdominal area of the patient.

(3) Continuous fluoroscopic imaging is commenced, thereby providing good images of the patient's spinal structures. Then, vertebral landmarks are located, bearing in mind that the renal arteries branch from the aorta at around L1, L2 (lumbar vertebrae 1-2) in the AP orientation.

(4) The Virtual Road Mapping System then overlays, on top of the live fluoroscopic images, virtual images from the virtual, patient-specific 3D model, with those images representing only the patient's bony spinal structures.

(5) The virtual images (from the virtual 3D model) of the patient's bony spinal structures are placed in proper registration with the real-time fluoroscope images of the patient's bony spinal structures, whereby the coordinate system of the virtual 3D model will be correlated to the coordinate system of the fluoroscope. This can be done using several methods, either in conjunction with one another or independently. Mathematically, a transformation is defined which maps the space of the virtual 3D model (derived from pre-acquired CT scan data) to the patient's space within the fluoroscope apparatus.

(a) In one form of the invention, registration is achieved by manual registration. By way of example but not limitation, such registration may be effected through visual inspection of the overlaid images.

Figure 4:
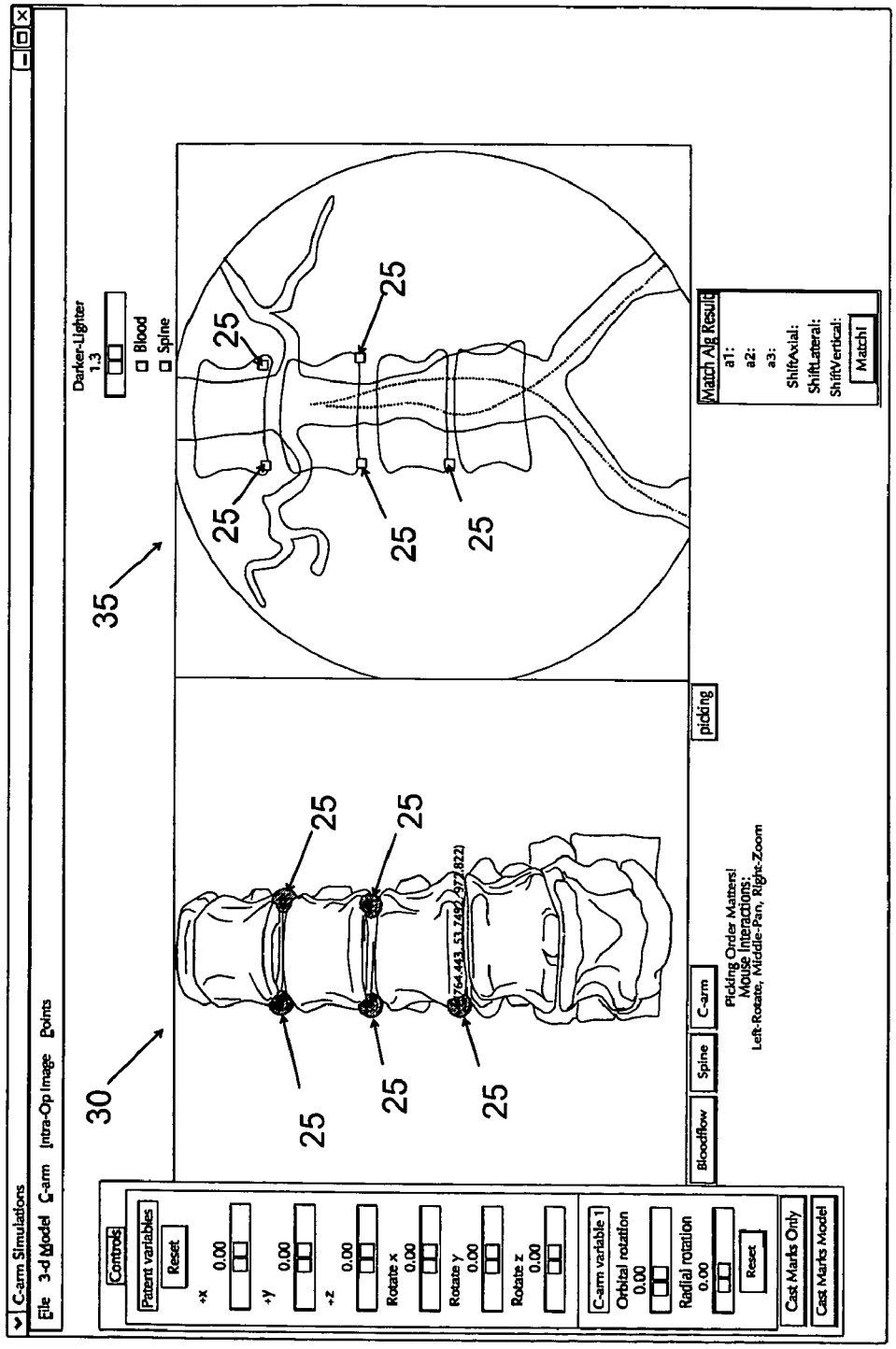
FIG. 4 is schematic view illustrating how fiducial points may be used to establish correspondence between (i) virtual images generated from the patient's CT-derived spine and blood flow data, and (ii) the composite images produced by datafusing the real-time fluoroscope images with the virtual images generated from the patient's CT-derived spine and blood flow data.

(b) In another form of the invention, registration is achieved by semi-automatic registration. By way of example but not limitation, such registration may be effected by establishing a number of landmark or fiducial points 25 that share correspondence between the virtual 3D model 30 (derived from the pre-acquired CT data) and the fluoroscopic image 35. See FIG. 4.

(c) In still another form of the invention, registration is achieved by automatic registration. By way of example but not limitation, such registration may be achieved through "vision-based" matching algorithms such as "Maximization of Mutual Information".

(6) Next, the spinal bones are imaged using fluoroscopy so as to create a standard mask image of the patient's vertebrae.

(7) The Virtual Road Mapping System is then configured to turn off the virtual images of the virtual bony structures and turn on the virtual images of the vascular structure, so as to show the blood flow (including the renal arteries) from the virtual 3D model overlaid on top of the live fluoroscopic image in a semi-transparent mode. Thus, there is provided a composite view simultaneously showing the patient's vascular structures from the virtual 3D model and the patient's bony structures from the real-time fluoroscopic image.

(7A) Then, the mask image is used to subtract out the bony structures from the composite view, whereby to produce the virtual road map which will be used by the surgeon.

(8) Next, various guidewires, device sheaths, catheters, etc. are deployed in the patient using the virtual road map provided by the Virtual Road Mapping System (i.e., by subtracting away the mask image, only the surgical devices and the semi-transparent blood flow rendering are presented as guidance for the renal artery position).

(9) Using the controls in the Virtual Road Mapping System, the optimal angle is set for visualizing the proximal neck of the AAA. The image of the virtual 3D structure for blood flow will adjust dynamically in response to the system controls so as to help in determining the best settings for the C-arm fluoroscope. Note that the MMS Preview™ software can also be used in advance to determine the best C-arm angles for stent deployment.

(10) Without moving the patient, the radial and orbital angles for C-arm fluoroscope are set to match the values previously determined using the Virtual Road Mapping System. If desired, an automated electro-mechanical assembly may be used to automatically set the radial and orbital values for the C-arm fluoroscope using the determinations made with the Virtual Road Mapping System.

(11) If necessary, the patient registration step may be repeated (e.g., using the bony landmarks and the standard fluoroscopic view of the vertebrae).

(12) At this point, the fluoroscope is now optimally positioned to view the proximal neck of the AAA and the stent device. A single contrast shot to produce a standard fluoroscopic road map view can be done at this time to guarantee accuracy immediately before deployment.

(13) The stent device is now deployed, and leaks are checked for using small squirts of contrast agent.

It should be noted that the methodology just described eliminates at least one "road map" view and can save the patient half of the otherwise required contrast.

Figure 5:
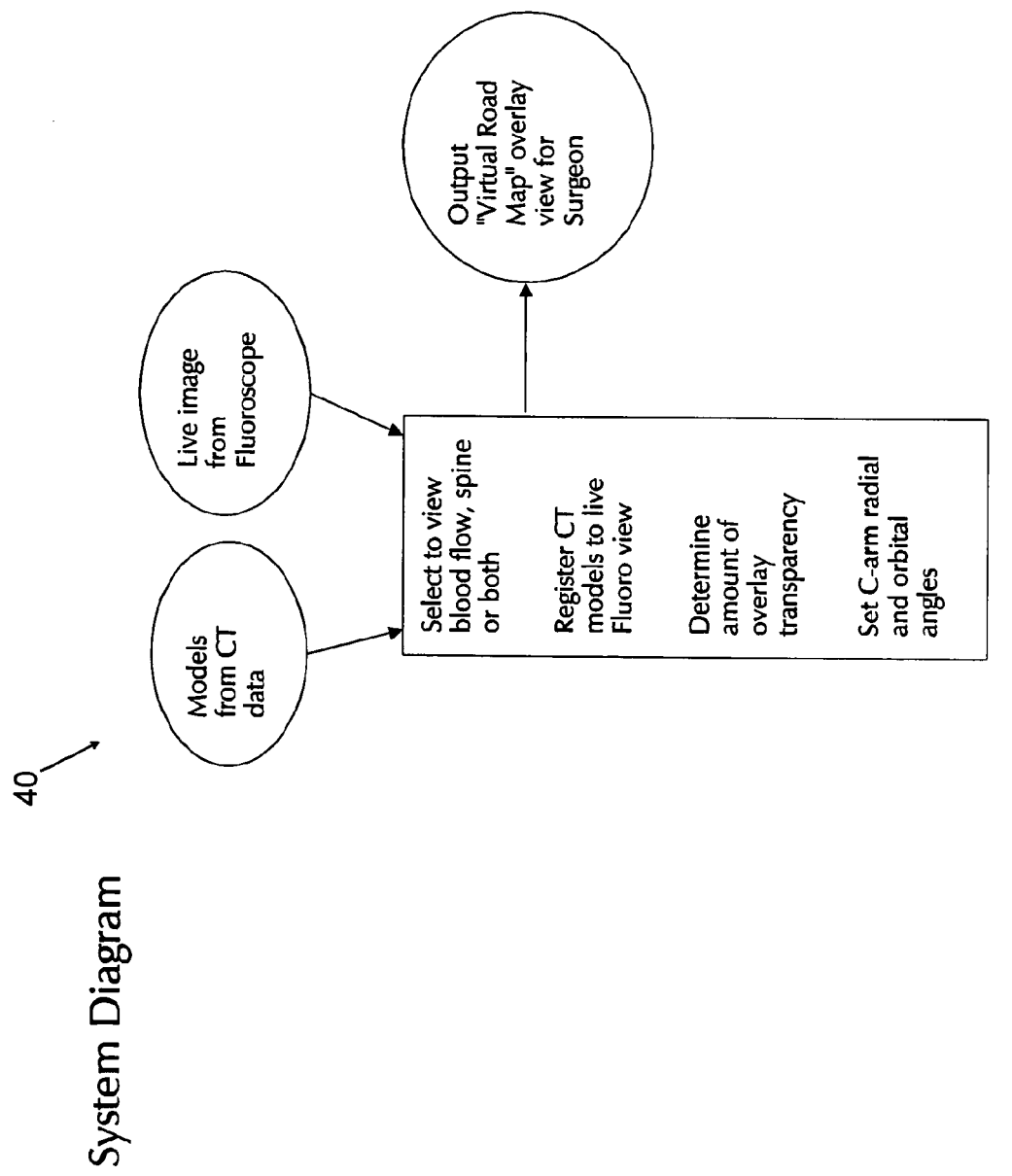
FIG. 5 is a schematic view showing a system diagram for one preferred embodiment of the present invention.

FIG. 5 shows a system diagram 40 for one preferred embodiment of the present invention.

MODIFICATIONS

It is to be understood that the present invention is by no means limited to the particular constructions herein disclosed and/or shown in the drawings, but also comprises any modifications or equivalents within the scope of the invention.

What is claimed is:

1. A method for visualizing anatomical structures, the method comprising the steps of:

(1) processing pre-acquired scanned patient-specific data so as to produce a virtual 3D model of anatomical structures of a patient, wherein processing is effected so that separate views of the patient's bone and blood flow structures can be generated;

(2) positioning a C-arm fluoroscope with standard Anterior-Posterior (AP) orientation relative to the patient;

(3) conducting fluoroscopic imaging so as to provide real-time images of the patient's bone structure;

(4) overlaying, on top of the fluoroscopic images, virtual images from the virtual 3D model, with those images representing only the patient's bone structure;

(5) placing the virtual images of the patient's bone structure generated from the virtual 3D model in registration with the fluoroscope images of the patient's bone structure, whereby a coordinate system of the virtual 3D model is correlated to a coordinate system of the fluoroscope;

(6) imaging the patient's bone structure using fluoroscopy so as to create a mask image of the patient's bone structure;

(7) turning off the virtual images of the virtual bone structure and turning on the virtual images of the blood flow structure, so as to show the blood flow structure from the virtual 3D model overlaid on top of the fluoroscopic images in a semi-transparent mode, thereby providing a composite view simultaneously showing the patient's blood flow structure from the virtual 3D model and the patient's bone structure from the fluoroscopic images;

(8) using the mask image to subtract out the bone structure from the composite view, whereby to produce the virtual road map which will be used by the surgeon; and (9) visualizing the virtual road map on a display monitor.

2. A method according to claim 1 wherein the pre-acquired scanned patient-specific data is obtained from apparatus selected from the group consisting of CT, CT-angiography and MRA.

3. A method according to claim 1 wherein the C-arm fluoroscope is configured to scan in a radial and an orbital direction.

4. A method according to claim 1 wherein placing the virtual images of the patient's bone structure in registration with the fluoroscope images of the patient's bone structure comprises manual registration.

5. A method according to claim 4 wherein manual registration comprises visually inspecting overlaid images.

6. A method according to claim 1 wherein placing the virtual images of the patient's bone structure in registration with the fluoroscope images of the patient's bone structure comprises semi-automatic registration.

7. A method according to claim 6 wherein semi-automatic registration comprises using landmark or fiducial points.

8. A method according to claim 1 wherein placing the virtual images of the patient's bone structure in registration with the fluoroscope images of the patient's bone structure comprises automatic registration of the fluoroscopic images with the virtual images of the patient's bone structure.

9. A method according to claim 8 wherein automatic registration comprises a vision-based matching algorithm.

10. A method according to claim 9 wherein the vision-based matching algorithm comprises a Maximization of Mutual Information algorithm.

11. A method according to claim 1 wherein the C-arm fluoroscope is positioned in the abdominal area.

12. A method according to claim 1 wherein the real-time images of the patient's bone structure comprise real-time images of the patient's spine.

* * * * *